United States Patent
Reinhardt et al.

(10) Patent No.: US 8,426,642 B2
(45) Date of Patent: Apr. 23, 2013

(54) METHOD FOR ISOLATING CONCENTRATED PARAFFIN SULFONIC ACIDS

(75) Inventors: Gerd Reinhardt, Kelkheim (DE); Peter Naumann, Taunusstein (DE); Lars Cuypers, Munich (DE)

(73) Assignee: Clariant Finance (BVI) Limited, Tortola (VG)

( * ) Notice: Subject to any disclaimer, the term of this patent is extended or adjusted under 35 U.S.C. 154(b) by 243 days.

(21) Appl. No.: 12/598,229

(22) PCT Filed: Apr. 29, 2008

(86) PCT No.: PCT/EP2008/003453
§ 371 (c)(1),
(2), (4) Date: Nov. 12, 2009

(87) PCT Pub. No.: WO2008/135198
PCT Pub. Date: Nov. 13, 2008

(65) Prior Publication Data
US 2010/0087674 A1    Apr. 8, 2010

(30) Foreign Application Priority Data
May 3, 2007   (DE) .......................... 10 2007 020 697

(51) Int. Cl.
*C07C 309/04*   (2006.01)
(52) U.S. Cl.
USPC .......................................... 564/121; 564/124
(58) Field of Classification Search .................. 562/121, 562/124
See application file for complete search history.

(56) References Cited

U.S. PATENT DOCUMENTS

| | | | | |
|---|---|---|---|---|
| 4,686,097 | A | * | 8/1987 | Horoldt et al. ................ 423/520 |
| 4,808,343 | A | * | 2/1989 | Pistorius ....................... 562/124 |
| 5,055,610 | A | * | 10/1991 | Borgarello et al. ........... 562/124 |
| 5,107,019 | A | * | 4/1992 | Gallistru et al. .............. 562/124 |

FOREIGN PATENT DOCUMENTS

| | | |
|---|---|---|
| DE | 0 735 096 | 12/1940 |
| DE | 0 907 052 | 8/1942 |
| DE | 0 910 165 | 4/1954 |
| DE | 1 139 116 | 11/1962 |
| DE | 2 045 087 | 3/1971 |
| DE | 2 139 477 | 2/1972 |
| DE | 2 730 245 | 7/1978 |
| DE | 3 301 727 | 7/1984 |
| EP | 0 131 913 | 1/1985 |
| EP | 0 158 235 | 10/1985 |
| EP | 0 268 224 | 5/1988 |
| EP | 0 402 978 | 12/1990 |
| EP | 0 430 352 | 6/1991 |
| FR | 1 603 096 | 4/1971 |
| GB | 1 204 514 | 9/1970 |
| GB | 1 358 095 | 6/1974 |
| GB | 1 532 207 | 11/1978 |

OTHER PUBLICATIONS

International Search Report for PCT/EP2008/003453, dated Nov. 12, 2008.
International Preliminary Report on Patentability for PCT/EP2008/003453, dated Nov. 19, 2009.
English Abstract for DE 0 735 096 dated Dec. 10, 1940.
English Abstract for DE 0 907 052 dated Aug. 1, 1942.
English Abstract for DE 0 910 165 dated Apr. 29, 1954.
English Abstract for DE 1 139 116 dated Nov. 8, 1962.
English Abstract for FR 1 603 096 dated Apr. 23, 1971.

* cited by examiner

*Primary Examiner* — Peter G O Sullivan
(74) *Attorney, Agent, or Firm* — Tod A. Waldrop

(57) ABSTRACT

The invention relates to a method for isolating concentrated paraffin sulfonic acids from reaction mixtures that are produced during the sulfoxidation of n-paraffins, from which a major part of the sulfuric acid and the paraffin was removed by phase separation and which contain, in addition to the free paraffin sulfonic acids, n-paraffins, water and optionally minor amounts of sulfuric acids. The method according to the invention is characterized by removing paraffin and optionally residual water by vacuum distillation. The paraffin sulfonic acids obtained by distillation have a content of more than 85% by weight of the active substance. The material is pale, odorless and low in sulfuric acid and paraffin.

10 Claims, No Drawings

METHOD FOR ISOLATING CONCENTRATED PARAFFIN SULFONIC ACIDS

The present invention relates to a method for isolating concentrated paraffin sulfonic acids from the reaction mixtures that are produced during the sulfoxidation of ($C_{10}$-$C_{22}$) paraffins, which comprises, after separating off sulfuric acid as far as possible, removing the residual paraffin and water from the reaction mixture by vacuum distillation.

Salts of the paraffin sulfonic acids have been used for many years in the detergents and cleaners industry, but also in the petrochemical sector. The large scale production of paraffin sulfonic acids takes place by sulfoxidation of long-chain ($C_{10}$-$C_{22}$) paraffins (e.g. DE 0 910 165). In order to obtain industrially useful products with surface-active properties from the reaction mixture that is produced during the sulfoxidation, it is necessary to remove dissolved sulfur dioxide, formed sulfuric acid and excess paraffins as completely as possible.

For this, various methods are described in the literature. Thus, for example, DE 0 907 052 describes a methanol/water method in which paraffin is separated off by extraction with hydrocarbons such as trimethylpentane. DE 0 910 165 protects a method in which paraffin is separated off after the sulfoxidation by adding methanol. After adding isooctane and concentrating the solution by evaporation at 120° C., a product phase was isolated which is composed of 70 to 75% paraffin sulfonic acids, 7-8% sulfuric acid and water. In DE 2 139 477, the paraffin is removed by adding methanol. The content of sulfuric acid is then reduced to a tolerable degree by adding heptanol. In DE 2 730 245 as well, paraffin is removed by adding methanol while, in a further step, the sulfuric acid is removed by adding butyl ether to the reaction mixture and phase separation. The isolated product phase consists of 65% paraffin sulfonic acid, 11% sulfuric acid and 24% water.

A further option for isolating paraffin sulfonic acids is described in DE 3 301 727, where, after separating off the sulfuric acid, the paraffin sulfonic acid is extracted with glycol. The product phase obtained in this way consists of 50 to 60% of paraffin sulfonic acid, 20 to 30% of sulfonic acid glycol ester, 10 to 20% glycol and water. Disadvantages of this extraction method are firstly the complex solvent recycling, the formation of undesired sulfonic esters and the low concentration of the resulting paraffin sulfonic acids.

A further way of separating off and purifying paraffin sulfonic acids is protected in EP 0 430 352. Here, firstly the sulfoxidation mixture is extracted with supercritical carbon dioxide to remove paraffin, then concentrated sulfuric acid is added and the mixture is subjected to an extraction with cyclohexane. In this method too, it is not possible to dispense with the use of a solvent. Moreover, the handling of supercritical carbon dioxide requires special apparatuses.

FR 1 603 096 proposes the treatment of the reaction mixture with oxygen-saturated water at 60 to 180° C., concentration and removal of the sulfuric acid, giving an approximately 40% strength paraffin sulfonic acid.

DE 2 045 087 recommends a steam distillation at 80 to 250° C. and 50 to 760 mm Hg, followed by the removal of sulfuric acid, the product obtained being an aqueous paraffin sulfonic acid with active contents of 70 to 80%. A disadvantage of this method has proven to be the thermal steam treatment of the paraffin sulfonic acid in the presence of sulfuric acid, and also the required amounts of steam, which preclude a commercialization of the method.

In the majority of the methods described, the separating off of the sulfuric acid from the paraffin sulfonic acid is only carried out in the last reaction stage, resulting, especially in the case of thermal methods, in undesired secondary reactions caused by sulfuric acid, which can considerably impair the quality of the paraffin sulfonic acids.

None of the described methods for isolating relatively long-chain paraffin sulfonic acids has hitherto been able to become established industrially because either the fraction of removed sulfuric acid and/or paraffins is too low, the expenditure for the distillative removal of the solvent used is too high, the active content of the resulting paraffin sulfonic acid was <80% or its quality was inadequate.

EP 0 131 913 indicates that the paraffin sulfonic acids present in the acidic reaction mixture decompose at temperatures above 100° C., with an onset of decomposition above just 50° C. being suspected.

It was an object of the invention to isolate concentrated paraffin sulfonic acids from sulfoxidation mixtures which have a low residual paraffin content and a low content of sulfuric acid.

Surprisingly, it has now been found that relatively long-chain paraffin sulfonic acids are thermally stable and can be separated off from paraffins by distillation if the majority of the sulfuric acid has been removed prior to the distillation step.

The invention provides a method for isolating concentrated paraffin sulfonic acids from reaction mixtures that are produced during the sulfoxidation of n-paraffins, from which a major part of the sulfuric acid and the paraffin has been removed by phase separation and which comprise, in addition to the free paraffin sulfonic acids, also n-paraffins, water and optionally small amounts of sulfuric acid. This method consists in removing the paraffin and optionally residual amounts of water by vacuum distillation. The concentrated paraffin sulfonic acid obtained in this way can then be bleached and/or neutralized with Na hydroxide or K hydroxide to obtain the corresponding paraffin sulfonates (alkane sulfonates).

Suitable starting materials for the method according to the present invention are the reaction mixtures as are obtained by methods known per se, for example in accordance with DE 0 735 096, DE 0 910 165 or DE 1 139 116, by sulfoxidation of n-paraffins. Firstly, by methods known per se, a major part of the excess n-paraffin and of the resulting sulfuric acid is removed from these reaction mixtures by means of phase separation before the distillation according to the present invention. The reaction mixture that remains, consisting of paraffin sulfonic acid, residual paraffin, water and small amounts of residual sulfuric acid, then serves as starting material for the method according to the invention.

The starting material used for the method of the present invention is generally composed of 10 to 50% paraffin sulfonic acids, 30 to 70% n-paraffins, 0 to 40% water and 0 to 5% sulfuric acid. Preferably, the starting material is composed of 12 to 40% paraffin sulfonic acids, 40 to 60% n-paraffins, 15 to 40% water and 0 to 3% sulfuric acid. If desired, in order to completely remove the sulfuric acid, it is possible for the starting material for the method of the present invention to be admixed as described in example 2 with alkaline earth metal salts, preferably calcium carbonate or calcium hydroxide, and for the precipitated alkaline earth metal sulfates to be filtered off.

If necessary, the starting material used can also be freed from low-boiling substances, such as, for example, water, prior to the vacuum distillation in a degassing stage. This can take place, as is known to the person skilled in the art, e.g.

using a falling-film evaporator or a flash box in the temperature range from 20 to 120° C., preferably 40 to 80° C., under reduced pressure.

To obtain the free paraffin sulfonic acids, the starting material described previously or the already largely dewatered variant is subjected to a vacuum distillation. The vacuum distillation is carried out at temperatures from 40 to 130° C., preferably 60 to 100° C., and pressures from $10^{-4}$ to 1 mbar, preferably $10^{-2}$ to 0.1 mbar. In order to avoid excessive heating of the product, short residence times during the separation are desired. Furthermore, it has proven to be advantageous, after removal of the paraffin has taken place, to cool the reaction bottom as quickly as possible to <80° C., preferably <60° C., in order to obtain a pale product. Under certain reaction conditions, it cannot be ruled out that anhydrides, esters, etc. will form as by-products in small amounts during the heating of the reaction mixture. In order to convert these compounds to the free paraffin sulfonic acid, it has proven to be advantageous to add 0.1 to 5% water to the reaction bottom (paraffin sulfonic acid) following the thermal separation.

Suitable apparatuses for the vacuum distillation are evaporators known to the person skilled in the art, e.g. thin-film evaporators, falling-film evaporators or short-path evaporators, as are currently supplied, for example, by Buss-SMS-Canzler, UIC, Gig Karassek or Gea Wiegand. For reasons of corrosion, particular demands are placed on the materials of the evaporator unit, and apparatuses made of Hastelloy, tantalum, glass, enamel or similarly corrosion-stable materials or coatings are preferably used.

To generate the required vacuum, it is possible to use, for example, liquid ring, rotary vane, annular piston, rotary piston, lobe, claw, scroll, membrane, reciprocating piston, turbomolecular, oil diffusion or oil-vapor-jet pumps, but also gas-binding vacuum pumps or suitable combinations of different vacuum pumps.

Depending on distillation conditions, the isolated paraffin sulfonic acid can have a dark color. If appropriate, the obtained paraffin sulfonic acid can therefore be treated after the distillation with bleaches, such as, for example, hydrogen peroxide. Here, 0.1 to 10% hydrogen peroxide are mixed at 10 to 60° C. with the paraffin sulfonic acid. The reaction time is 10 min to 6 h depending on temperature. It has proven to be advantageous to stabilize the bleached paraffin sulfonic acid by adding 1 to 15% water. The bleached paraffin sulfonic acid can then be converted to a salt, added to a detergent and cleaner formulation or be used as free acid in concentrated or diluted form.

An essential advantage of the procedure according to the invention is considered to be that it is possible using the described method to economically isolate pale, low-odor paraffin sulfonic acids that are low in sulfuric acid and paraffin.

In this way, paraffin sulfonic acids are obtained with a content of active substance of more than 85%, preferably more than 90%. The residual paraffin content is less than 5%, preferably less than 3%, and the content of sulfuric acid is below 5% by weight, preferably below 3% by weight.

EXAMPLES

Example 1

In a 1 l loop reactor, 1 l/h of $C_{14}/C_{17}$-paraffin were mixed with water and gassed with 670 l/h (STP) of sulfur dioxide and 330 l/h (STP) of oxygen. The reaction mixture was irradiated using a medium-pressure mercury lamp (TQ 150 Heraeus) at a temperature of 38° C. until 0.6% water, 93.8% $C_{14}/C_{17}$-paraffin, 4.1% $C_{14}/C_{17}$-paraffin sulfonic acid and 1.5% $H_2SO_4$ were present in the reaction mixture. Sulfuric acid separated out of this mixture. The upper phase was isolated and admixed with water such that an upper phase of paraffin separated out. The lower phase consisted of 29.1% $C_{14}/C_{17}$-paraffin sulfonic acid, 49.0% $C_{14}/C_{17}$ paraffin, 20.5% water and 1.4% sulfuric acid.

The lower phase was dewatered at 1.5 mbar and 70° C. using a falling-film evaporator, where the intermediate in the bottom consisted of 38% $C_{14}/C_{17}$-paraffin sulfonic acid, 60% $C_{14}/C_{17}$ paraffin, 0.1% water and 1.8% sulfuric acid. The intermediate was then distilled at 0.05 mbar and 100° C. in a short-path evaporator, where a dark brown product bottom of composition 94.2% $C_{14}/C_{17}$-paraffin sulfonic acid, 1.2% $C_{14}/C_{17}$ paraffin, <0.1% water and 1.2% sulfuric acid was obtained.

Example 2

The procedure was carried out and the reaction mixture was worked up analogously to example 1. After separating off the paraffin and the majority of the sulfuric acid, a phase of the following composition was obtained: 14.8% $C_{14}/C_{17}$-paraffin sulfonic acid, 49.1% $C_{14}/C_{17}$-paraffin, 34.9% water and 1.2% sulfuric acid.

1000 g of the product phase were admixed with 13 g of calcium carbonate and stirred for four hours at room temperature. The precipitated calcium sulfate was filtered off. The filtrate consisted of 14.9% $C_{14}/C_{17}$-paraffin sulfonic acid, 49.5% $C_{14}/C_{17}$-paraffin, 35.2% water and 0.4% sulfuric acid. The filtrate was dewatered at 1.5 mbar and 70° C. using a falling-film evaporator, where the intermediate in the bottom consisted of 23.7% $C_{14}/C_{17}$-paraffin sulfonic acid, 75.4% $C_{14}/C_{17}$-paraffin, 0.3% water and 0.6% sulfuric acid.

The intermediate was then distilled at 0.1 mbar and 100° C. in a short-path evaporator, where a red-brown product bottom of composition 94.6% $C_{14}/C_{17}$-paraffin sulfonic acid, 2.8% $C_{14}/C_{17}$-paraffin, <0.1% water and 2.4% sulfuric acid was obtained.

Example 3

For the distillation, a reaction mixture of composition 36.4% $C_{14}/C_{17}$-paraffin sulfonic acid, 58.2% $C_{14}/C_{17}$-paraffin, 4.4% water and 1.9% sulfuric acid was used.

The thermal stability of the reaction mixture was tested beforehand using differential thermoanalysis (DTA) in a closed crucible at a heating rate of 3 K/min. In order to prevent catalytic wall influences during the measurement, exclusively glass crucibles were used. Sample preparation was carried out under air, although the effect is negligible since the energy content of a possible oxidation reaction is, at around –20 J/g, insignificant on account of the overlaid oxygen partial pressure. In the investigated temperature range from 25 to 400° C., the investigation of the sample revealed a slightly exothermic decomposition reaction above 280° C. On account of the low energy release of –50 J/g and the low reactivity, this cannot lead to a critically self-accelerating decomposition reaction.

The reaction mixture was distilled at $3*10^{-3}$ mbar and 110° C. in a glass thin-film evaporator. In the distillation bottom, a dark brown product of composition 93.5% $C_{14}/C_{17}$-paraffin sulfonic acid, 1.5% $C_{14}/C_{17}$-paraffin, <0.1% water and 4.9% sulfuric acid was obtained.

Example 4

100 g of dark brown alkanesulfonic acid of composition 93.5% $C_{14}/C_{17}$-paraffin sulfonic acid, 1.5% $C_{14}/C_{17}$-paraffin, <0.1% water and 4.9% sulfuric acid were admixed at room temperature with 3 g of hydrogen peroxide (30% strength) and stirred for 4 hours at room temperature. 15 g of distilled water were then added. The product was a pale yellow liquid with the composition 79.2% $C_{14}/C_{17}$-paraffin sulfonic acid, 1.3% $C_{14}/C_{17}$-paraffin, 15.3% water and 4.2% sulfuric acid.

The invention claimed is:

1. A method for isolating concentrated paraffin sulfonic acids from reaction mixtures that are produced during the sulfoxidation of n-paraffins, from which a major part of the sulfuric acid and the paraffin has been removed by phase separation and which comprise, in addition to the free paraffin sulfonic acids, also n-paraffins, water and optionally small amounts of sulfuric acid, comprising the step of removing paraffin and optionally residual water from the reaction mixture by vacuum distillation, wherein the vacuum distillation is carried out at a pressure from $10^{-3}$ mbar to 1 mbar.

2. The method as claimed in claim 1, wherein the starting material for the vacuum distillation consists of 10 to 50% paraffin sulfonic acids, 30 to 70% n-paraffins, 0 to 40% water and 0 to 5% sulfuric acid.

3. The method as claimed in claim 1, wherein the starting material for the vacuum distillation consists of 12 to 40% paraffin sulfonic acids, 40 to 60% n-paraffins, 15 to 40% water and 0 to 3% sulfuric acid.

4. The method as claimed in claim 1, wherein the vacuum distillation is carried out at a temperature from 50 to 150° C.

5. The method as claimed in claim 1, wherein the vacuum distillation is carried out at a temperature from 80 to 120° C.

6. The method as claimed in claim 1, wherein the vacuum distillation is carried out at a pressure from $10^{-2}$ mbar to 0.1 mbar.

7. The method as claimed in claim 1, wherein the vacuum distillation is carried out in a thin-film evaporator.

8. The method as claimed in claim 1, wherein the vacuum distillation is carried out in a short-path evaporator.

9. The method as claimed in claim 1, wherein the starting material is dewatered prior to the vacuum distillation.

10. The method as claimed in claim 1, wherein the sulfuric acid in the starting material is neutralized with alkaline earth metal salts prior to the vacuum distillation and the alkaline earth metal sulfates that are produced are separated off from the starting material.

* * * * *